(12) United States Patent
Johnson

(10) Patent No.: US 6,283,986 B1
(45) Date of Patent: *Sep. 4, 2001

(54) METHOD OF TREATING WOUNDS WITH ULTRAVIOLET C RADIATION

(75) Inventor: Robert G. Johnson, Franklinton, NC (US)

(73) Assignee: Medfaxx, Inc., Wake Forest, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/515,155

(22) Filed: Feb. 29, 2000

Related U.S. Application Data

(60) Provisional application No. 60/122,263, filed on Mar. 1, 1999.

(51) Int. Cl.$^7$ ........................................... A61N 1/00
(52) U.S. Cl. .................................... 607/94; 607/88
(58) Field of Search .......................... 607/94, 88

(56) References Cited

U.S. PATENT DOCUMENTS 5,871,522 * 2/1999 Sentilles ................................ 604/94

OTHER PUBLICATIONS

E. L. Nussbaum et al; *Comparison of Ultrasound/Ultraviolet–C and Laser for Treatment of Pressure Ulcers in Patients With Spinal Cord Injury*; Physical Therapy vol. 74, No. 9 (Sep. 1994).

Mike Enghauser et al; *Exposure to Germinicidal Ultraviolet Radiation at Duke University Medical Centerl North*, (Apr. 28, 1993) pp. 4–29.

A. S. Carlsson et al; *Ultraviolet radiation and air contamination during total hip replacement*, Journal of Hospital Infection (1986) 7, pp. 176–184.

M. Berg–Perier et al; *Ultraviolet Radiation and Ultra–clean Air Enclosures in Operating Rooms*, Ultraviolet Radiation in Operating Rooms, The Journal of Arthroplasty, vol. 7, No. 4; (Dec. 1992) pp. 457–463.

M. Berg–Perier; *Ultraviolet Light in Operating Rooms*, (1992) pp. 8–93.

T. A. Conner–Kerr; *The Effects of Ultraviolet Radiation on Antibiotic–Resistant Bacteria In Vitro*, Ostomy/Wound Management, vol. 44, No. 10, (Oct. 1998) pp. 50–56.

\* cited by examiner

*Primary Examiner*—Raymond Henley, III
(74) *Attorney, Agent, or Firm*—Myers Bigel Sibley & Sajovec

(57) ABSTRACT

A method of treating wounds includes the step of applying UVC radiation to the wound for a time and at a proximity and intensity sufficient to have a bacteriocidal effect. The method is particularly effective when carried out with a UVC lamp having an intensity of between 5 and 20 $\mu W/cm^2$, with a duration of between about 5 seconds and 1 minute and a proximity to the wound of between about ¼ and 3 inches from the wound being preferred. It has been observed that such application of UVC radiation can kill up to 100 percent of the microorganisms present in a wound, thereby enabling the wound to heal free of infection.

19 Claims, No Drawings

METHOD OF TREATING WOUNDS WITH ULTRAVIOLET C RADIATION

RELATED APPLICATIONS

This application claims priority from U.S. Provisional Patent Application Ser. No. 60/122,263, filed Mar. 1, 1999.

FIELD OF THE INVENTION

The present invention relates generally to medical treatments, and more specifically to the treatment of wounds.

BACKGROUND OF THE INVENTION

The treatment of infected open wounds has long been a troublesome area of medical practice. An initial stage of wound healing is characterized by the formation of granulation tissue, which is a matrix of collagen, fibronectin, and hyaluronic acid carrying macrophages, fibroblasts and neovasculature that forms the basis for subsequent epithelialization of the wound. Infection (including that by bacteria, mold spores, yeast, and virus) can hinder the formation of granulation tissue within the wound, thereby inhibiting healing.

Many infected wounds, and in particular those infected with bacteria, are treated with antibiotics. These therapeutic agents can be applied topically or administered via some other route, such as orally. Unfortunately, due to the constant use (and perhaps the overuse) of antibiotics, some bacteria have evolved to become resistant to antibiotics. As a result of the therapeutic failure of some front-line antibiotics, the medical community is faced with developing new patient treatment options.

It has been known for some time that ultraviolet (UV) light can have antimicrobial effects. See, e.g., Licht, Therapeutic Electricity and Ultraviolet Radiation (Waverly Press, 1967). Early experiments demonstrated that properties of sunlight (either a heating effect or a property of the sun's rays itself) could prevent bacterial growth. Later, UV light was shown to be bacteriocidal to many bacteria, including *Mycobacterium tuberculosis, Staphlococcus, Streptococcus, Bacillus anthrasis,* and *Shigella dysenteriae.* UW light has also been a common treatment for tuberculosis of the skin. Id.

UV light can be divided into different classes based on wavelength, including ultraviolet A (UVA) at about 350 nm, ultraviolet B (UVB) at about 300 nm, and ultraviolet C (UVC) at about 250 nm. Not unexpectedly, the effectiveness of UV light in producing biological changes can differ at different wavelengths.

For wound healing, the use of UV light is attractive in that it is a non-pharmalogical treatment that is non-invasive to the wound. It has been demonstrated that UV light can increase epithelial cell turnover, release prostaglandin precursors and histamines, increase vascular permeability, accelerate DNA synthesis, and inactivate bacterial cells. However, UVA and UVB have been shown to cause damage to the skin, particularly in the form of sunburn and blistering, each of which would be undesirable, particularly to an open wound; also, these forms of UV radiation have been demonstrated to be carcinogenic.

SUMMARY OF THE INVENTION

In view of the foregoing, it is an object of the present invention to provide a non-pharmacologic, non-invasive treatment of wounds.

It is also an object of the present invention to provide a wound treatment that can address infections of microorganisms that are antibiotic-resistant.

It is a further object to provide such a treatment that lacks the undesirable side effects of UVA and UVB light.

These and other objects may be satisfied by the present invention, which is directed to a method of treating wounds through the application of UVC radiation to the wound for a time and at a proximity and intensity sufficient to have a bacteriocidal effect. The method is particularly effective when carried out with a UVC lamp having an intensity of between 5 and 20 $W/cm^2$, with a duration of between about 5 seconds and 1 minute and a proximity to the wound of between about ¼ and 3 inches from the wound being preferred. It has been observed that such application of UVC radiation can kill up to 100 percent of the microorganisms present in a wound, thereby enabling the wound to heal free of infection.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As noted above, the present invention employs UVC radiation in the treatment of wounds. As used herein, "UVC radiation" is intended to encompass ultraviolet radiation having a wavelength of between about 240 and 260 nm. UVC radiation having with a wavelength of between about 243 and 255 nm is preferred; in same embodiment, a wavelength of between about 245 and 247 nm is more preferred, as it has been observed that the bacteriocidal effect of the UVC radiation tends to peak at this wavelength range. In other embodiments, a wavelength of between about 253 and 255 nm may be more preferred.

Although the inventor does not wish to be bound by any theory of operation, it is believed that the application of UVC radiation to bacteria is bacteriocidal because of the close similarity of the UVC wavelength to the maximum absorption rate of DNA (which is about 260 nm). As such, the application of UVC can cause photochemical changes in the DNA that either cause immediate death or impair the reproduction of the organism. Because the reproductive cycle of most microorganisms is much faster than that of normal cells (particularly when the microorganism is in an infectious state), they are much more susceptible to the harmful effect of the UVC than the surrounding cells.

The wounds that can be treated by the present invention can be any wounds that are susceptible to bacterial infection. Thus, wounds suitable for treatment with the present invention include surgical wounds, pressure sores or ulcers, lacerations, epidermal trauma, and others having bacteria residing therein or in the surrounding area. They can include both surface wounds (i.e., those present in the skin) and internal wounds, such as those created in surgical procedures. For internal wounds, it is preferred that the wounds be exposed for facilitated application of the UVC radiation to the wound. Also, the infection in the wounds may be localized or systemic infections. It is also contemplated that the treatment can be used on both human subjects and non-human subjects (i.e., for veterinary use).

The UVC radiation applied to the wound is typically supplied by a UVC germicidal lamp, although other UVC radiation sources may also be suitable. A germicidal UVC lamp is generally of the configuration of a fluorescent lamp and requires the same type of peripheral or auxiliary equipment. A UVC lamp typically contains no phosphor, but has a drop of liquid mercury dispersed in an argon gas vacuum. The mercury floats within the argon; when electricity is introduced, the mercury atoms discharge UVC radiation at approximately 260 nm. The UVC lamp will typically include a special glass bulb, cover or lens that allows transmission of most of the UVC radiation generated by the mercury arc (up to 74 percent of the UVC energy can be transmitted through the glass). A particularly suitable UVC lamp is the V-254 lamp, available from MedFaxx, Inc., Raleigh, N.C.

Because of the varied treatment regimes for different microorganisms, it may be desirable for the UVC radiation source to include means for varying intensity and/or wavelength within the UVC range. Also, an integral timer can be included to time the duration of UVC radiation application.

The UVC lamp or other UVC radiation source should provide UVC radiation at an intensity that enables it to have a bacteriocidal effect on the microorganism(s) to which it is applied. Typically, an intensity of between about 5 and 20 $\mu W/cm^2$ is suitable, with an intensity of between about 15 and 16 $\mu W/cm^2$ being preferred.

During application of UVC radiation to the wound, the UVC lamp or other UVC radiation source should be positioned sufficiently proximate to the wound so as to have a bactericidal effect. This position is typically between about ¼ and 3 inches from the wound, with a distance of between about ½ and 1 inches being preferred.

Application of UVC radiation to a wound is performed for a time sufficient to have a bacteriocidal effect on the wound. Typically, the duration of application is between about 5 seconds and 1 minute, with a duration of between about 5 and 30 seconds being preferred. Of course, the duration may be varied depending on the type and character of the wound, the microorganism to be eliminated, and the intensity and position of the UVC source.

The types of microorganisms that can be treated with the treatment method of the present invention include bacteria, yeast, mold spores, viri, and protozoa. Exemplary lists of microorganisms are set forth in Tables 1–5; those skilled in this art will appreciate that these lists are exemplary only and that other microorganisms may also be suitable for treatment.

TABLE 1

| ORGANISM | ENERGY ($\mu W\text{-}s/cm^2$) | |
|---|---|---|
|  | 90% kill | 100% kill |
| Bacillus anthracis | 4520 | 8700 |
| S. enteritidis | 4000 | 7600 |
| B. Megaterium sp. (veg.) | 1300 | 2500 |
| B. Megaterium sp. (spores) | 2730 | 5200 |
| B. paratyphusus | 3200 | 6100 |
| B. subtilis | 5800 | 11000 |
| B. subtilis spores | 11600 | 22000 |
| Clostridium tetani | 13000 | 22000 |
| Corynebacterium diphtheriae | 3370 | 6500 |
| Eberthella typosa | 2140 | 4100 |
| Escherichia coli | 3000 | 6600 |
| Micrococcus candidus | 6050 | 12300 |

TABLE 1-continued

| ORGANISM | ENERGY ($\mu W\text{-}s/cm^2$) | |
|---|---|---|
|  | 90% kill | 100% kill |
| Micrococcus sphaeroides | 10000 | 15400 |
| Myrobacterium tuberculosis | 6200 | 10000 |
| Neisseria catarrhalis | 4400 | 8500 |
| Phtomonas tumeficiens | 4400 | 8500 |
| Proteus vulgaris | 3000 | 6600 |
| Pseudomonas aeruginosa | 5500 | 10500 |
| Pseudomonas fluorescens | 3500 | 6600 |
| S. typhimurium | 8000 | 15200 |
| Salmonella typhosa-typhoid Fever | 2150 | 4100 |
| Salmonella paratyphi-enteric Fever | 3200 | 6100 |
| Sarcina lutea | 19700 | 4200 |
| Serratia marcescens | 2420 | 3400 |
| Shigella dysenteriae-Dysentery | 2200 | 4200 |
| Shigella flexneri-Dysentery | 1700 | 3400 |
| Shigella paradysenteriae | 1680 | 3400 |
| Spirillum rubrum | 4400 | 6160 |
| Staphylococcus albus | 1840 | 5720 |
| Staphylococcus aureus | 2600 | 6600 |
| Streptococcus hemolyticus | 2160 | 5500 |
| Streptococcus lactis | 6150 | 8800 |
| Streptococcus viridans | 2000 | 3800 |
| Vibrio comma-Cholera | 3375 | 6500 |
| Leptospira canicola-Infectious Jaundice | 3150 | 6000 |

*tests carried out at 253.7 nm UVC

TABLE 2

| YEAST | ENERGY ($\mu W\text{-}s/cm^2$) | |
|---|---|---|
|  | 90% kill | 100% kill |
| Saccharomyces ellipsoideus | 6000 | 13200 |
| Saccharomyces sp. | 8000 | 17600 |
| Saccharamyces carevisiae | 6000 | 13200 |
| Brewers Yeast | 3300 | 6600 |
| Bakers Yeast | 3900 | 8800 |
| Common yeast cake | 6000 | 13200 |

*tests carried out at 253.7 nm UVC

TABLE 3

| MOLD SPORES | COLOR | ENERGY ($\mu W\text{-}s/cm^2$) | |
|---|---|---|---|
|  |  | 90% kill | 100% kill |
| Penicillium roqueforti | Green | 13000 | 26400 |
| Penicillium expansum | Olive | 13000 | 22000 |
| Penicillium digitatum | Olive | 44000 | 88000 |
| Aspergillus glaucus | Bluish green | 44000 | 88000 |
| Aspergillus flavus | Yellowish green | 60000 | 99000 |
| Aspergillis niger | Black | 132000 | 330000 |
| Rhisopus nigricans | Black | 111000 | 220000 |
| Mucor racemosus A | White gray | 17000 | 352000 |
| Mucor racemosus B | White gray | 17000 | 352000 |
| Oospora lactis | White | 5000 | 11000 |

*tests carried out at 253.7 nm UVC

TABLE 4

| VIRUS | ENERGY ($\mu$W-s/cm$^2$) | |
|---|---|---|
| | 90% kill | 100% kill |
| Bacteriophage (*E.Coli*) | 2600 | 6600 |
| Infectious Hepatitis | 5800 | 8000 |
| Influenza | 3400 | 6600 |
| Poliovirus-Paliomyelitis | 3150 | 6000 |
| Tobacco mosaic | 240000 | 440000 |

*tests carried out at 253.7 nm UVC

TABLE 5

| PROTOZOA | ENERGY (#W-s/cm2) | |
|---|---|---|
| | 90% kill | 100% kill |
| Paramecium | 110000 | 200000 |
| Nematode eggs | 4000 | 92000 |
| *Chlorella vulgaris* | 12000 | 22000 |

*tests carried out at 253.7 nm UVC

It has been observed that different microorganisms may be more susceptible to eradication by different wavelengths within the UVC radiation range. For example, vancomycin-resistant *Enterococcus faecalis* (VRE) and methicillin-resistant *Staphlococcus aureus* (MRSA) have both proven to be very susceptible to UVC having a wavelength of 246 nm. This result is very encouraging, as these microorganisms are particularly troublesome to control in the wounds of human patients with pressure ulcers.

Note that Tables 1–5 also include recommended UVC radiation energy levels to destroy 90 percent and 100 percent of these microorganisms. This information can be used to calculate application duration and frequency. For example, according to Table 3 the mold spore *Aspergillis niger* requires 330,000 $\mu$W-s/cm$^2$ for complete destruction. Assuming a UVC output of 2,250 $\mu$W per cm$^2$ of wound area, a 146 second application interval is needed for total destruction of the microorganism. This can be accomplished in a single 146 second treatment, or, alternatively, in three 49 second treatments.

Prior to the application of UVC radiation to the wound, it may be useful to rinse the wound surface. Doing so can increase the ability of the UVC radiation to reach the pathogens and maximize pathogen exposure to UVC. Stimulating the intact skin surrounding the wound prior to treatment may also improve results. It is also recommended that the surrounding tissue be protected (such as by a protective gel).

In practice, it has been observed that UVC radiation can have the following effects on wounds: increased epithelial cell turnover; epidermal cell hyperplasia; increased DNA synthesis facilitated by prostaglandin precursors release; histamine release to increase skin blood flow; increased vascular leakiness; bacterial cell inactivation; increased vitamin D production; accelerated sloughing of necrotic tissue; and erythema and increased UV absorption by nucleic acids. Notably, application of UVC radiation does not cause significant permanent skin pigmentation; this is in contrast to UVA and UVB exposure, which can cause such an effect. As a result, subsequent UVC radiation treatments need not be increased in intensity or duration in order to overcome a pigmentation effect. In addition, the application of UVC may have a positive effect on healing after treatments cease. It is theorized that pathogens in the underlying tissues are migrating to the surface more rapidly and accelerating an immune response than in the absence of treatment (as, given the short wavelength of UVC, no penetration of the underlying tissue would be expected).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention.

That which is claimed is:

1. A method of treating wounds, comprising the step of applying ultraviolet C radiation to the wound for a time and at a proximity and intensity sufficient to have a bacteriocidal effect, wherein said wound is selected from the group consisting of: pressure sores; ulcers; lacerations; and epidermal trauma.

2. The method defined in claim 1, wherein said ultraviolet C radiation is applied to the wound at an intensity of between 5 and 20 $\mu$W/cm$^2$.

3. The method defined in claim 1, wherein said ultraviolet C radiation is applied to the wound for a duration of between about 5 seconds and 1 minute.

4. The method defined in claim 1, wherein said ultraviolet C radiation is applied to the wound at a proximity to the wound of between about ¼ and 3 inches.

5. The method defined in claim 1, wherein said ultraviolet C radiation having a wavelength of between about 245 and 247 nanometers is applied.

6. The method defined in claim 1, wherein said ultraviolet C radiation having a wavelength of between about 253 and 255 nanometers is applied.

7. The method defined in claim 1, wherein said ultraviolet C radiation is applied with an ultraviolet radiation C germicidal lamp.

8. The method defined in claim 1, wherein said wound is contaminated with at least one pathogen selected from the group consisting of: bacteria, yeast, mold spores, viri, and protozoa.

9. The method defined in claim 1, further comprising the step of rinsing the wound prior to said applying step.

10. A method of treating wounds, comprising the step of applying ultraviolet C radiation to the wound at an intensity of between 5 and 20 $\mu$W/cm$^2$ for a duration of between about 5 seconds and 1 minute and at a proximity to the wound of between about ¼ and 3 inches.

11. The method defined in claim 10, wherein said ultraviolet C radiation having a wavelength of between about 245 and 247 nanometers is applied.

12. The method defined in claim 10, wherein said ultraviolet C radiation having a wavelength of between about 253 and 255 nanometers is applied.

13. The method defined in claim 10, wherein said wound is selected from the group consisting of: surgical wounds; pressure sores; ulcers; lacerations; and epidermal trauma.

14. The method defined in claim 10, wherein said ultraviolet C radiation is applied with an ultraviolet radiation C germicidal lamp.

15. The method defined in claim 10, wherein said wound is contaminated with at least one pathogen selected from the group consisting of: bacteria, yeast, mold spores, viri, and protozoa.

16. The method defined in claim 10, further comprising the step of rinsing the wound prior to said applying step.

17. A method of treating wounds, comprising the step of applying ultraviolet C radiation to the wound at an intensity of between 5 and 20 $\mu$W/cm$^2$ for a duration of between about 5 seconds and 1 minute and at a proximity to the wound of between about ¼ and 3 inches;

wherein said ultraviolet C radiation is applied with an ultraviolet radiation C germicidal lamp; and wherein said wound is selected from the group consisting of: surgical wounds; pressure sores; ulcers; lacerations; and epidermal trauma.

18. A method of treating wounds, comprising the steps of:
stimulating intact skin surrounding the wound; then
applying ultraviolet C radiation to the wound for a time and at a proximity and intensity sufficient to have a bacteriocidal effect.

19. A method of treating wounds, comprising the steps of:
stimulating intact skin surrounding the wound; then
applying ultraviolet C radiation to the wound at an intensity of between 5 and 20 $\mu$W/cm$^2$ for a duration of between about 5 seconds and 1 minute and at a proximity to the wound of between about ¼ and 3 inches.

* * * * *

UNITED STATES PATENT AND TRADEMARK OFFICE
CERTIFICATE OF CORRECTION

PATENT NO. : 6,283,986 B1
DATED : September 4, 2001
INVENTOR(S) : Johnson

It is certified that error appears in the above-identified patent and that said Letters Patent is hereby corrected as shown below:

Column 5,
Line 17, heading title of table 5 should appear as follows:

ENERGY
($\mu$W-s/cm$^2$)

Signed and Sealed this

Thirtieth Day of April, 2002

Attest:

JAMES E. ROGAN
Director of the United States Patent and Trademark Office

Attesting Officer